(12) United States Patent
Lauchner

(10) Patent No.: US 9,924,931 B2
(45) Date of Patent: Mar. 27, 2018

(54) CANNULA AND METHODS OF USE

(71) Applicant: Kyphon SARL, Neuchatel (CH)

(72) Inventor: Craig E. Lauchner, Sunnyvale, CA (US)

(73) Assignee: Kyphon SÀRL, Neuchâtel (CH)

( * ) Notice: Subject to any disclaimer, the term of this patent is extended or adjusted under 35 U.S.C. 154(b) by 99 days.

(21) Appl. No.: 14/694,717

(22) Filed: Apr. 23, 2015

(65) Prior Publication Data

US 2015/0366582 A1 Dec. 24, 2015

Related U.S. Application Data

(63) Continuation-in-part of application No. 14/309,604, filed on Jun. 19, 2014, now Pat. No. 9,675,333.

(51) Int. Cl.
*A61B 17/02* (2006.01)
*A61B 17/34* (2006.01)
*A61B 90/30* (2016.01)
*A61B 17/00* (2006.01)
*A61B 17/70* (2006.01)

(52) U.S. Cl.
CPC ...... *A61B 17/0218* (2013.01); *A61B 17/0293* (2013.01); *A61B 17/3421* (2013.01); *A61B 17/3423* (2013.01); *A61B 90/30* (2016.02); *A61B 17/3439* (2013.01); *A61B 17/7074* (2013.01); *A61B 2017/00477* (2013.01); *A61B 2017/00951* (2013.01); *A61B 2017/00991* (2013.01); *A61B 2017/346* (2013.01); *A61B 2017/3407* (2013.01); *A61B 2017/3433* (2013.01); *A61B 2017/3458* (2013.01); *A61B 2017/3492* (2013.01); *A61B 2090/309* (2016.02)

(58) Field of Classification Search
CPC .......... A61M 25/02; A61M 2025/0206; A61B 17/3415; A61B 17/3417; A61B 17/3423; A61B 17/3431; A61B 17/3439
USPC .......................... 600/214, 215, 216, 219, 234
See application file for complete search history.

(56) References Cited

U.S. PATENT DOCUMENTS

| | | | |
|---|---|---|---|
| 2,697,433 A | 12/1954 | Zehnder | |
| 4,222,375 A * | 9/1980 | Martinez | A61B 1/07 600/249 |
| 4,484,913 A * | 11/1984 | Swauger | A61M 5/00 128/DIG. 26 |
| 4,608,977 A | 9/1986 | Brown | |
| 5,197,971 A * | 3/1993 | Bonutti | A61B 17/0218 604/105 |
| 5,201,742 A | 4/1993 | Hasson | |
| 5,540,675 A | 7/1996 | Hasson | |
| 5,690,607 A * | 11/1997 | Chin | A61B 17/0218 600/204 |
| 5,772,654 A | 6/1998 | Leyva | |
| 8,308,740 B2 | 11/2012 | Tolley et al. | |
| 8,361,091 B2 | 1/2013 | Schein et al. | |
| 8,500,759 B2 | 8/2013 | Koyfman et al. | |
| 8,603,078 B2 | 12/2013 | Stefanchik et al. | |

(Continued)

*Primary Examiner* — Anu Ramana

(57) ABSTRACT

A surgical instrument includes a cannula and a member coupled to the cannula. The member includes a first locking element. The surgical instrument further includes a patient attachable ring having a second locking element configured to engage the first locking element to fix the cannula relative to the patient attachable ring. Systems and methods are disclosed.

17 Claims, 8 Drawing Sheets

(56) References Cited

U.S. PATENT DOCUMENTS

2006/0224044 A1 10/2006 Marchek et al.
2009/0326462 A1 12/2009 Wingardner, III et al.

* cited by examiner

CANNULA AND METHODS OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Cannulas may be employed during a surgical treatment to provide access and visualization of a surgical site. Such cannulas space apart and support tissue and/or other anatomical structures to expose anatomical structures adjacent the surgical site and/or provide a surgical pathway to the surgical site.

During certain procedures, patients may be conscious and, as a result, these patients can move, forcing their back muscles to contract. Such contractions can push a cannula dorsally, which can cause bleeding in a working zone and a need to push the cannula ventrally. As a surgeon manipulates a cannula, a hand is used to wag and hold the top of the cannula. However, the cannula may slip out of the position set by the surgeon if not held securely in place by hand. This disclosure describes an improvement over prior art technologies as it, among other things, provides a means to hold a cannula after it is wagged, thus freeing the surgeon's off hand, that would otherwise be required to hold the cannula in the position set by the surgeon.

SUMMARY

Presently disclosed is a surgical instrument, comprising a cannula; a collar coupled to the cannula, the collar comprising a first locking element; and a patient attachable ring comprising a second locking element configured to engage the first locking element at a fixed junction to control the movement of the cannula within the patient attachable ring. The first and second locking elements can be detachable from one another. A portion of the first locking element can be disposed within the second locking element to prevent the cannula from moving radially about the patient attachable ring in some instruments disclosed. The cannula can be axially translatable relative the collar.

Also disclosed is a surgical instrument wherein the first and second locking elements define a sliding dovetail joint. There are some instruments wherein the first locking element can be a tapered tenon and the second locking element can be a mortise that slidingly engages the tenon such that the tenon and the mortise define a sliding dovetail joint. The first locking element can be a tapered tenon and the second locking element can comprise a plurality of sets each comprising a plurality of mortises that are in communication with one another, and the tenon slidingly engaging with one of the mortises to define a sliding dovetail joint in other instruments. The plurality of sets can be positioned radially about the patient attachable ring.

There is also a surgical instrument wherein the first locking element comprises a fishbone configuration comprising a plurality of extensions and the second locking element comprises a plurality of slots about the patient attachable ring.

Presently disclosed is a surgical instrument, wherein the first locking element comprises an elongate body with a control ring at an end opposite the collar and the second locking element comprises a plurality of distinct points of engagement. The elongate body in some instruments can include spaced apart projections extending therefrom and the distinct points of engagement comprise slots to receive the projections. In other instruments the elongate body can be positioned within one of the slots.

There are instruments disclosed herein where the collar engages the cannula to prevent axial translation of the collar relative the cannula. In some instruments an outer surface of the cannula comprises a helical thread form configured to engage tissue. In some other instruments the cannula comprises a light source. The cannula can be expandable in some instruments.

Also presently disclosed are methods of using the cannula positioning systems disclosed herein. The systems can comprise a cannula, a collar comprising a first locking element, and a patient attachable ring comprising a second locking element. The method comprises coupling the collar to the proximal end of the cannula, positioning the cannula using the collar, and engaging the first and second locking elements together to position the cannula within the patient attachable ring. In some methods, the first and second locking elements are engaged together at a fixed junction.

BRIEF DESCRIPTION OF THE DRAWINGS

The present disclosure will become more readily apparent from the specific description accompanied by the following drawings, in which.

DETAILED DESCRIPTION

Figure 1:
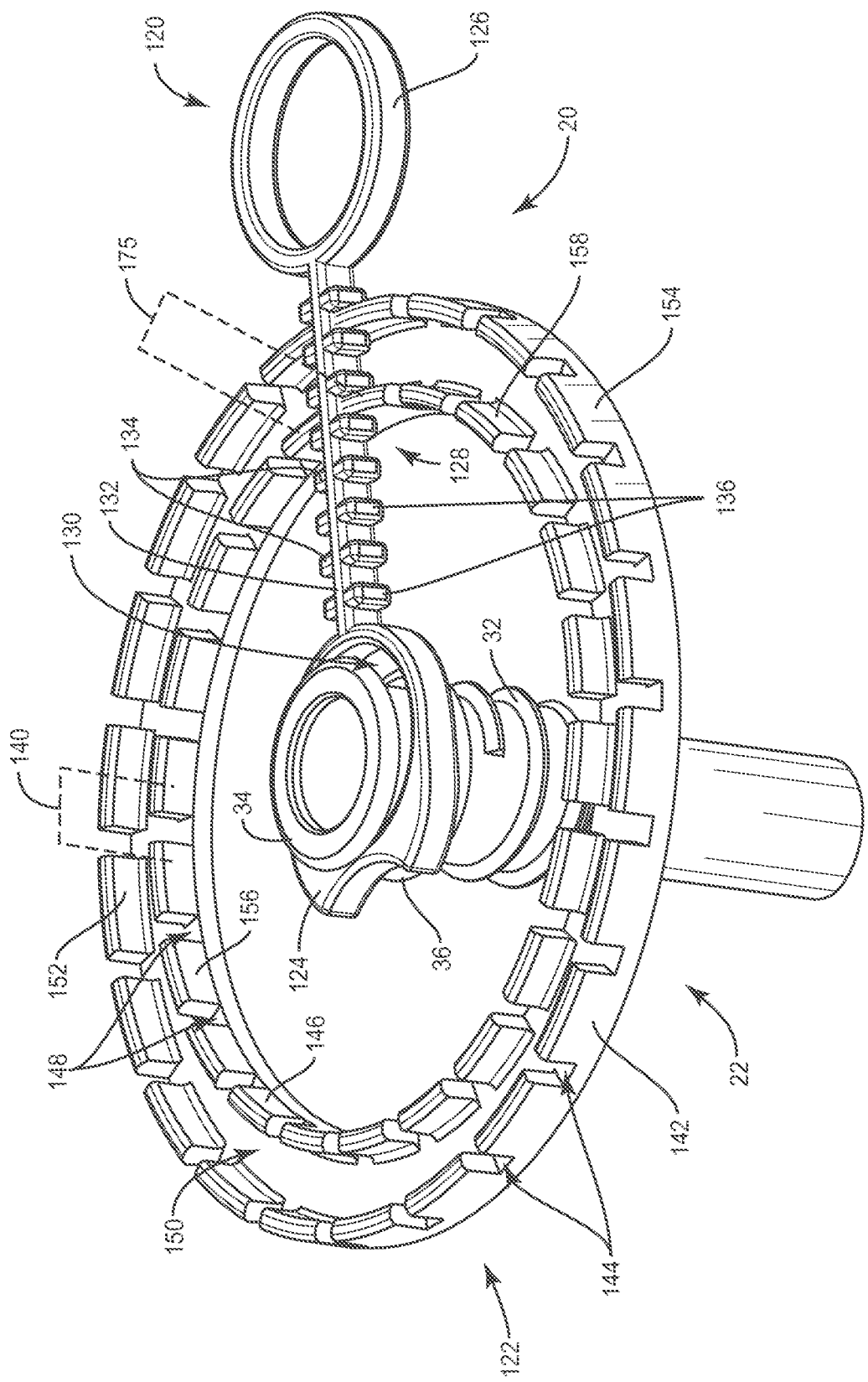
FIG. 1 is a top, perspective view of components of a surgical system in accordance with the principles of the present disclosure.

Cannulas may be employed during a surgical treatment to provide access and visualization of a surgical site. Such cannulas space apart and support tissue and/or other anatomical structures to expose anatomical structures adjacent the surgical site and/or provide a surgical pathway to the surgical site.

Cannulas are typically tubes including a lumen having a fixed diameter, which require an incision having a diameter that is larger than the diameter of the lumen, in order to insert the cannula into the anatomy of a patient. Expandable cannulas, on the other hand, move from one configuration, in which vertical members of a cannula define a lumen having a first, relatively small diameter for insertion into the patient's anatomy. Following insertion of the cannula into the patient's anatomy, the vertical members of the cannula are moved relative to one another such that the lumen defined by the vertical members of the cannula expands to have a second, larger diameter to provide an enlarged access portal for the insertion of surgical instruments therethrough. At least in certain circumstances, this allows the diameter of the incision to be less than the second, larger diameter of the lumen defined by the vertical members of the cannula, thus reducing trauma.

Whether an expandable cannula or a non-expandable cannula is used during a procedure, there may be a need to hold the cannula in a position in which the cannula is wagged to by a surgeon. This may be particularly important in procedures in which a patient remains at least partially conscious and, as a result, has a tendency to move during the procedure. The surgeon typically must use one hand to hold the cannula in a position in which the cannula was wagged by the surgeon, thus preventing the surgeon from using that hand for other purposes. The present disclosure is thus directed to cannula positioning systems having a wag and hold feature that holds the cannula in the position in which the cannula was wagged to by the surgeon, thus freeing the surgeon's off hand for other purposes.

The cannula positioning system may include a ring, which is attached to the patient by an adhesive. The ring is connected to the cannula by a connecting member such that the position of the cannula can be selectively adjusted relative to the ring. This configuration allows the surgeon to wag the cannula to a selected position and then engage the connecting member with the ring to fix the cannula in the selected position. In one embodiment, the cannula is axially translatable within the connecting member. In one embodiment, the connecting member includes a dovetailed hook that is configured to be received with a dovetailed groove in the ring to removably connect the connecting member with the ring, as will be discussed. In one embodiment, the connecting member has a fishbone configuration defined by a plurality of extensions and the ring includes a plurality of slots. The extensions are configured to be received within the slots to connect the connecting member with the ring, as will also be discussed.

The cannula may create an anchor by screwing the cannula over a dilator to secure the cannula in place in tissue. The cannula may be expanded after the cannula is screwed over the dilator, to further secure the cannula. The cannula may be circumferentially continuous, eliminating the need for time consuming bleeding control. This feature allows a surgeon, such as, for example, a physician to save a good deal of time by reducing the need for cauterizing tools. This feature also allows the surgeon to accurately limit the expanded size of the cannula.

The exemplary embodiments of a surgical system and related methods of use disclosed are discussed in terms of cannulas for the treatment of musculoskeletal disorders and more particularly, in terms of a surgical system and method for accessing a surgical site to facilitate treatment.

The present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. The present disclosure may be employed with other osteal and bone related applications, including those associated with diagnostics and therapeutics. The disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures.

The components of surgical system can be fabricated from biologically acceptable materials suitable for medical applications, including metals, synthetic polymers, ceramics and bone material and/or their composites, depending on the particular application and/or preference of a surgeon. For example, the components of surgical system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

System 20 comprises a cannula 22. System 20 may include features configured to help prevent dorsal movement of cannula 22 caused by movement of a patient, for example, who is awake and/or at least partially conscious. In one embodiment, shown in FIGS. 1-3, the features include a collar 120 configured to connect a patient attachable ring 122 to cannula 22. Collar 120 comprises a first end defining an engagement portion 124, an opposite second end defining a control ring 126 and an intermediate section positioned between engagement portion 124 and control ring 126 that defines a first locking element 128. The intermediate section comprises an elongate body with spaced apart projections 134, 136 extending therefrom. First locking element 128 is defined at least in part by spaced apart projections 134, 136.

Engagement portion 124 comprises an inner surface defining a bore 130 configured for disposal of cannula 22. In particular, cannula 22 is positioned through bore 130 such that engagement portion 124 is positioned between a proximal flange 34 of a sleeve 30 of cannula 22 and a distal flange 36 of sleeve 30 such that the inner surface of engagement portion 124 engages an outer surface of sleeve 30. Bore 130 may have a maximum diameter that is less than that of proximal flange 34 when engagement portion 124 is in an unstressed state such that engagement portion 124 must be stretched to enlarge the diameter of bore 130 to dispose cannula 22 within bore 130. Engagement portion 124 may comprise a material capable of elastic deformation such that bore 130 will return to its original diameter (the diameter of bore 130 before engagement portion 124 was stretched) after stress (stretching forces) are removed to prevent engagement portion 124 from disengaging cannula 22 unintentionally. Engagement portion 124 may have a thickness that is less than the distance between proximal flange 34 and distal flange 36 such that cannula is axially translatable relative to collar 120 when cannula 22 is disposed within bore 130. Engagement portion 124 may have a thickness that is equivalent or approximately equivalent to the distance between proximal flange 34 and distal flange 36 such that cannula 22 is prevented from translating axially relative to collar 120 when cannula 22 is disposed within bore 130.

Control ring 126 of collar 120 defines a loop configured for gripping by hand. When cannula 22 is positioned within bore 130, a surgeon may place a finger within the loop of control ring 126 and move his or her finger to move collar 120 and cannula 22 relative to patient attachable ring 122. The second end of collar 120 may have other configurations to facilitate control & movement of the collar 120 and cannula 22 relative to patient attachable ring 122. Such configurations may include any ergonomically designed end, such as a tab or a rod.

First locking element 128 has a fishbone configuration defined by a body 132. Body 132 includes a plurality of spaced apart first projections 134 extending from one side of body 132 and a plurality of spaced apart second projections 136 extending from an opposite side of body 132 such that each first projection 134 is aligned with one of second projections 136.

Patient attachable ring 122 is configured to be adhered to the skin of a patient. A tacky or sticky material may be applied to a bottom surface 138 of patient attachable ring 122 (FIG. 3) to facilitate attachment of patient attachable ring 122 to the skin of the patient. The tacky or sticky material may be a liquid adhesive, a paste or a solid material, such as, for example, adhesive tape or double-sided adhesive tape. Bottom surface 138 may have various surface configurations, such as, for example, smooth, to prevent irritation or injury and/or surface configurations to enhance attachment to the skin of the patient, such as, for example, rough, arcuate, undulating, porous, semi-porous, dimpled, polished and/or textured.

Patient attachable ring 122 comprises a second locking element 140 configured to engage first locking element 128 at a fixed junction 175 to fix collar 120 relative to patient attachable ring 122. In one embodiment, first locking element 128 is disposed within second locking element 140 to prevent cannula 22 from moving radially about patient attachable ring 122. First and second locking elements 128, 140 are detachable from one another. Second locking element 140 is defined by a first wall 142 including a plurality of spaced apart first slots 144 and a second wall 146 defining a plurality of spaced apart second slots 148. First and second walls 142, 146 are spaced apart from one another by a channel 150. Each first slot 144 is aligned with one of second slots 148. In one embodiment, second locking element 140 comprises a plurality of distinct points of engagement that are defined at least in part by slots 144, 148. Slots 144, 148 are configured to receive projections 134, 136. In some embodiments, at least a portion of the elongate body with spaced apart projections 134, 136 extending therefrom is positioned within at least one of slots 144, 148 when projections 134, 136 are received within slots 144, 148.

Body 132 of first locking element 128 is configured to be positioned within one of first slots 144 and one of second slots 148 to engage first locking element 128 with second locking element 140 at fixed junction 175 in a manner that fixes collar 120 relative to patient attachable ring 122. When body 132 is positioned within one of first slots 144 and one of second slots 148, a first one of first projections 134 and a first one of second projections may engage an inner surface 152 of first wall 142, a second one of first projections 134 and a second one of second projections 136 engage an outer surface 154 of first wall 142, a third one of first projections 134 and a third one of second projections 136 engages an inner surface 156 of second wall 146 and a fourth one of first projections 134 and a fourth one of second projections 136 engage an outer surface 158 of second wall 146.

Figure 5:
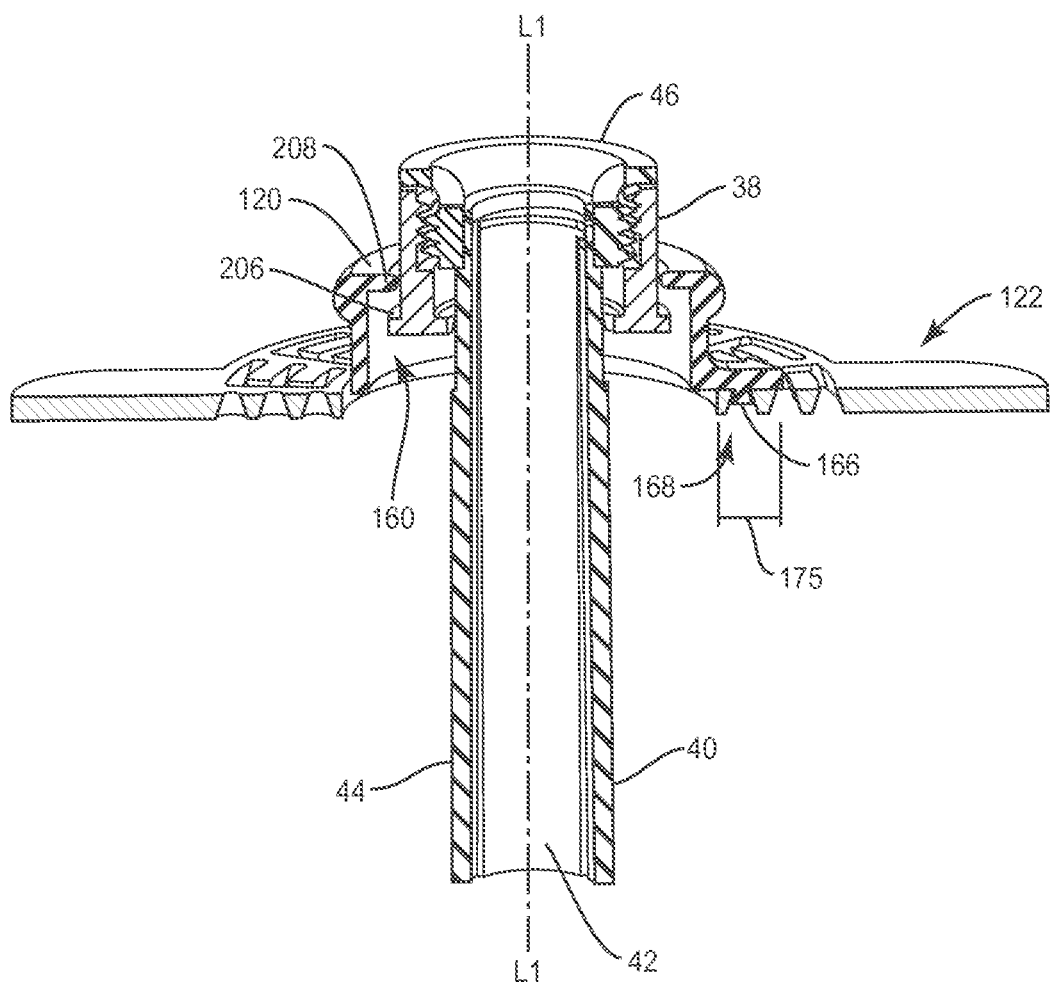
FIG. 5 is a perspective, cross sectional view of components of one embodiment of the system shown in FIG. 4.
Figure 6:
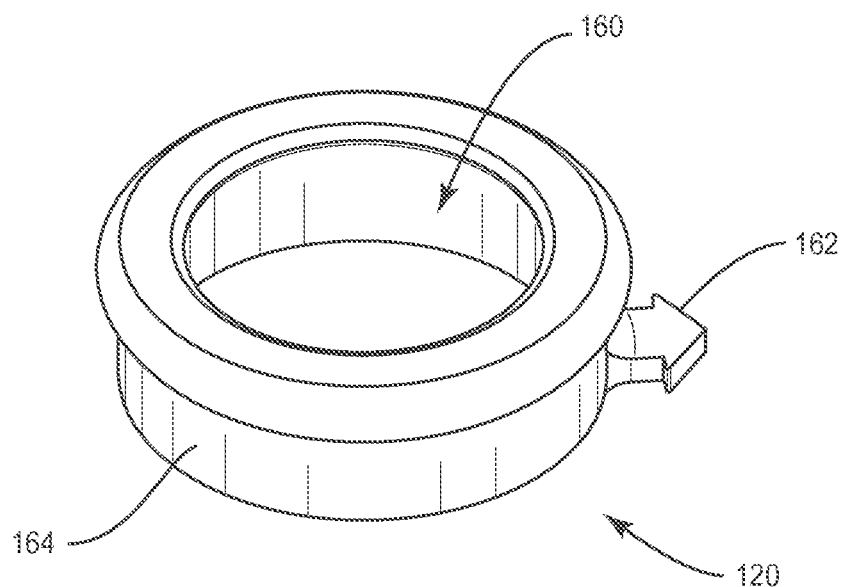
FIG. 6 is a top, perspective view of a component of one embodiment of the system shown in FIG. 4.
Figure 7:
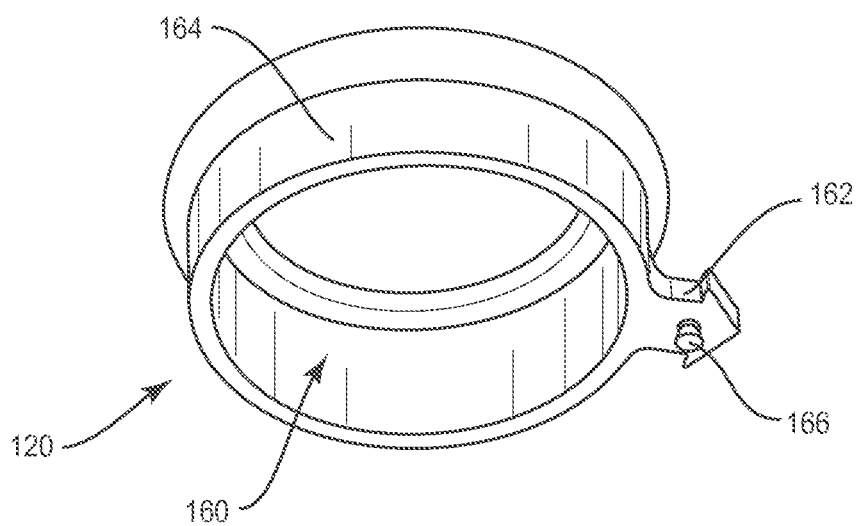
FIG. 7 is a bottom, perspective view of a component of one embodiment of the system shown in FIG. 4.

In one embodiment, shown in FIGS. 4-10, system 20 includes a cannula 22 and a collar 120 configured to connect a patient attachable ring 122 to cannula 22. The cannula depicted in FIGS. 4-5 happen to be expandable but other embodiment may comprise non expandable cannulas. As shown in FIGS. 6 and 7, collar 120 comprises an inner surface defining a pathway 160. A holding member 38, a first vertical member 40, a second vertical member 42 and a third vertical member 44 of cannula 22 are disposed in pathway 160 such that an assembly of holding member 38, first vertical member 40, second vertical member 42 and third vertical member 44 can translate axially within pathway 160, as shown in FIG. 5. In some embodiments, collar 120 engages cannula such that the assembly of holding member 38, first vertical member 40, second vertical member 42 and third vertical member 44 is prevented from translating axially within pathway 160.

Figure 10:
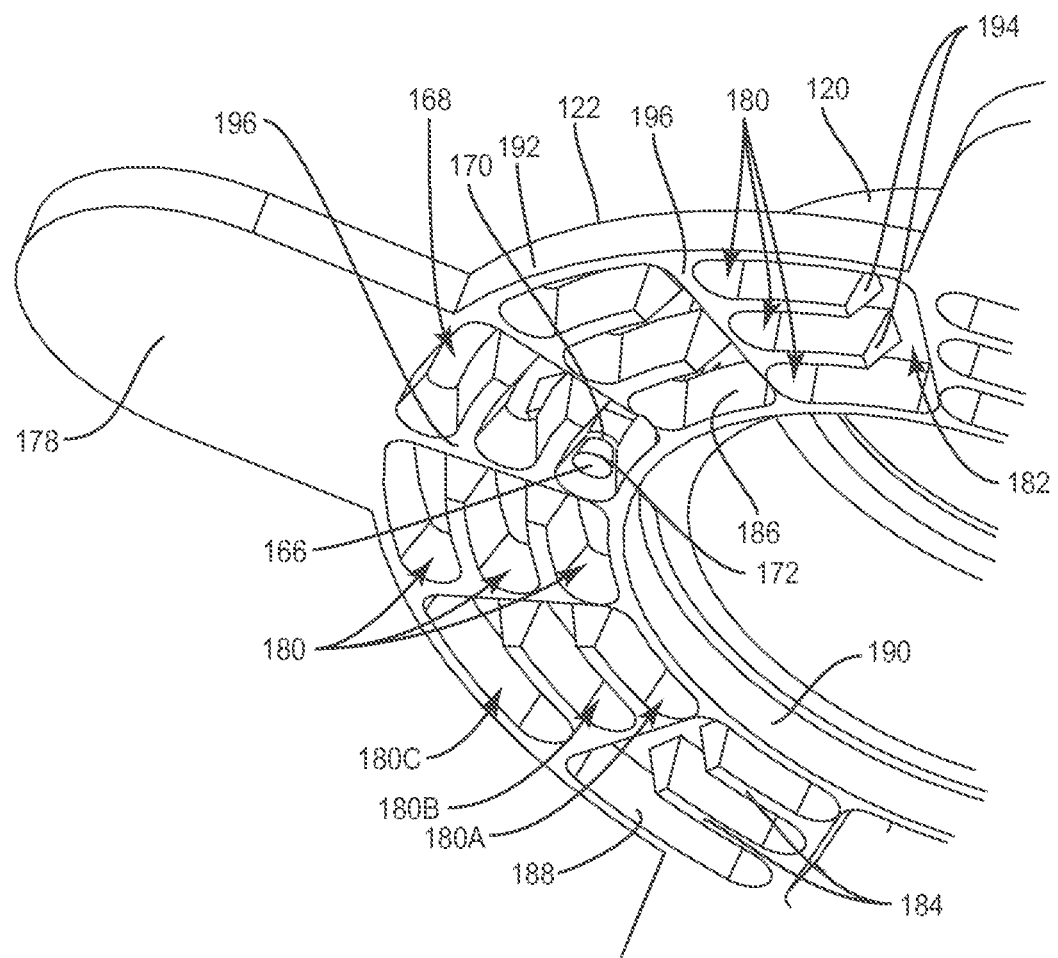
FIG. 10 is a bottom, perspective view of components of one embodiment of the system shown in FIG. 4

Collar 120 of system 20 comprises an extension 162 projecting outwardly from a body 164 of collar 120, as shown in FIGS. 6 and 7. Extension 162 comprises a first locking element 166 configured to engage a second locking element 168 of patient attachable ring 122 at a fixed junction 175 to fix collar 120 relative to patient attachable ring 122. As shown in FIG. 10, first locking element 166 includes a first portion 170 extending from extension 162 having a first width or diameter and a second portion 172 extending from first portion 170 having a second width or diameter that is greater than the first width or diameter. That is, a maximum width or diameter of second portion 172 is greater than a maximum width or diameter of first portion 170. First locking element 166 is tapered from second portion 172 to first portion 170 to define a tapered tenon. First and second locking elements 166, 168 are detachable from one another. In one embodiment, first locking element 166 is disposed in second locking element 168 to prevent cannula 22 from moving radially about patient attachable ring 122.

Figure 8:
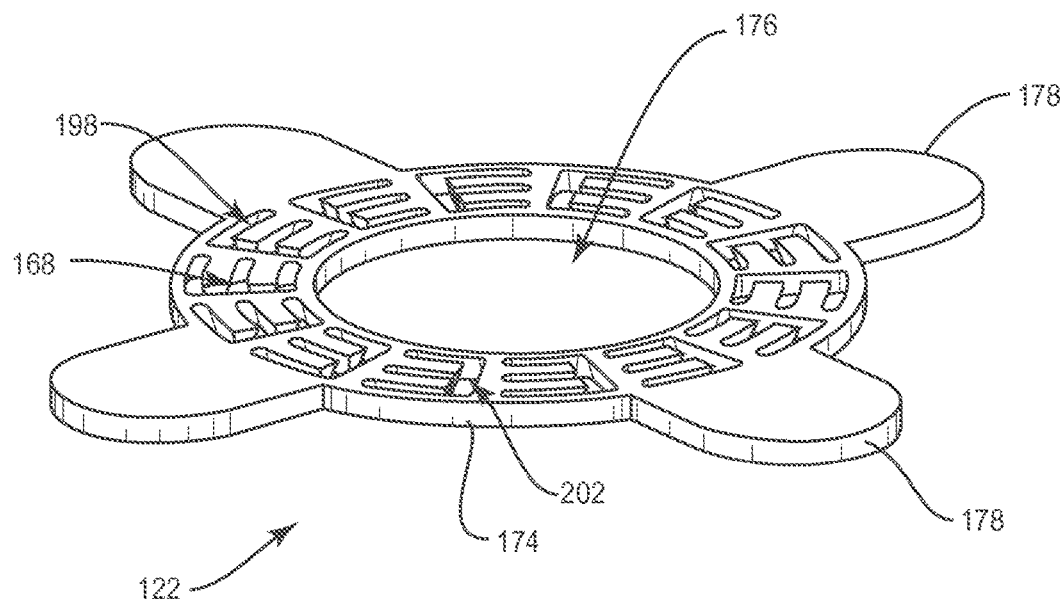
FIG. 8 is a top, perspective view of a component of one embodiment of the system shown in FIG. 4.
Figure 9:
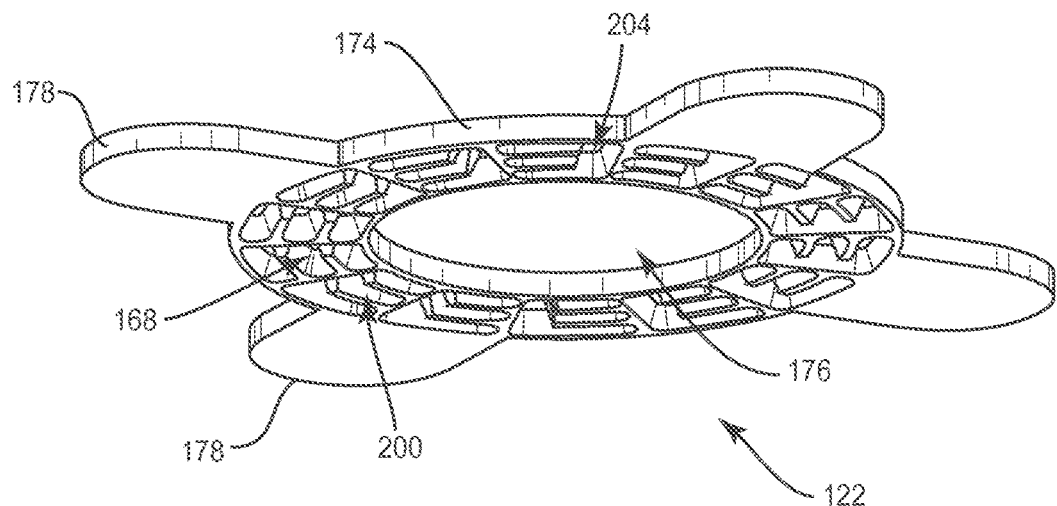
FIG. 9 is a bottom, perspective view of a component of one embodiment of the system shown in FIG. 4.

As shown in FIGS. 8 and 9, patient attachable ring 122 of system 20 comprises a body 174 that includes second locking element 168 extending through an upper surface of body 174 and an opposite lower surface of body 174. Second locking element 168 may be a mortise. There may be a plurality of mortises of varying or uniform diameters and dimensions in some embodiments. Body 174 may be circular and may include an inner surface defining a pathway 176. Patient attachable ring 122 includes a plurality of straps 178 extending outwardly from body 174 of patient attachable ring 122. Patient attachable ring 122 can include one or a plurality of straps 178. Patient attachable ring 122 may include a plurality of second locking elements 168. That is, patient attachable ring 122 may comprise a plurality of sets of second locking elements 168. The sets of second locking element 168 may be positioned radially about patient attachable ring 122. As shown in FIG. 10, second locking elements 168 may each include a plurality of mortises, such as, for example, grooves 180 each extending in a common or like direction and a single mortise, such as, for example, groove 182 that extends transversely through each of grooves 180 in a respective second locking element 168 in a direction that is transverse to the common or like direction. Grooves 180, 182 of a respective second locking element 168 are defined by a pair of fingers 184 and inner surfaces 186, 188 of inner and outer walls 190, 192 of patient attachable ring 122. End surfaces 194 of fingers 184 are angled relative to upper and/or lower surfaces of body 174 of patient attachable ring 122 to facilitate engagement with first locking element 166 of collar 120. In one embodiment, second locking element 168 comprises a plurality of distinct points of engagement defined at least in part by grooves 180, 182.

Second locking elements 168 of patient attachable ring 122 are spaced apart from one another by transverse walls 196 of patient attachable ring 122. Grooves 180 of second locking elements 168 each have a first opening 198 that extends through a top surface of patient attachable ring 122, as shown in FIG. 8. First openings 198 each have a third width or diameter. Grooves 180 each have a second opening 200 opposite first opening 198 that extends through a lower surface 124 of patient attachable ring 122, as shown in FIG. 9. Second openings 200 each have a fourth width or diameter that is greater than the third width or diameter. First and second openings 198, 200 are defined by fingers 184, inner surface 186 of inner wall 190 and/or inner surface 188 of outer wall 192, as shown in FIG. 10. The third width or diameter is less than the second width or diameter of second portion 172 of first locking element 166 and greater than the first width or diameter of first portion 170 of first locking element 166 and the fourth width or diameter is greater than the second width or diameter of second portion 172.

Grooves 182 each have a first opening 202 extending through the top surface of patient attachable ring 122, as shown in FIG. 8. First openings 202 each have a fifth width or diameter. Grooves 182 each have a second opening 204 opposite first opening 202 extending through the bottom surface of patient attachable ring 122, as shown in FIG. 9. Second openings 2014 each have a sixth width or diameter. The sixth width or diameter is greater than the fifth width or diameter due to the angled configuration of surfaces end surfaces 194 of fingers 184. The fifth and sixth widths or diameters are greater than the second width or diameter of second portion 172 of first locking element 166 and the first width or diameter of first portion 170 of first locking element 166 such that second portion 172 can be inserted axially through first opening 198 and slid laterally into one of grooves 180, 182. First and second locking elements 166, 168 form a dovetail joint, such as, for example a sliding dovetail joint at fixed junction 175.

In assembly, operation and use, surgical system 20, similar to that described above, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Embodiments of the present invention help prevent dorsal movement of cannulas, including non-expandable, expandable, and the like. The present invention provides an anchor to prevent unintended movement of the cannula. This secure anchor is created by screwing cannula 22 into a suitable location within the patient's body. For instance, a sequential dilator system may be used to create an access opening to the spine. Cannula 22 can be secured by screwing it over the last sequential dilator, securing it in place in neighboring muscle tissue. Cannula 22 may be secured in the neighboring muscle tissue by engaging the neighboring muscle tissue with a thread 32 on an outer surface of sleeve 30 of cannula 22, shown in FIG. 3. In some embodiments, thread 32 is a helical thread form.

Figure 2:
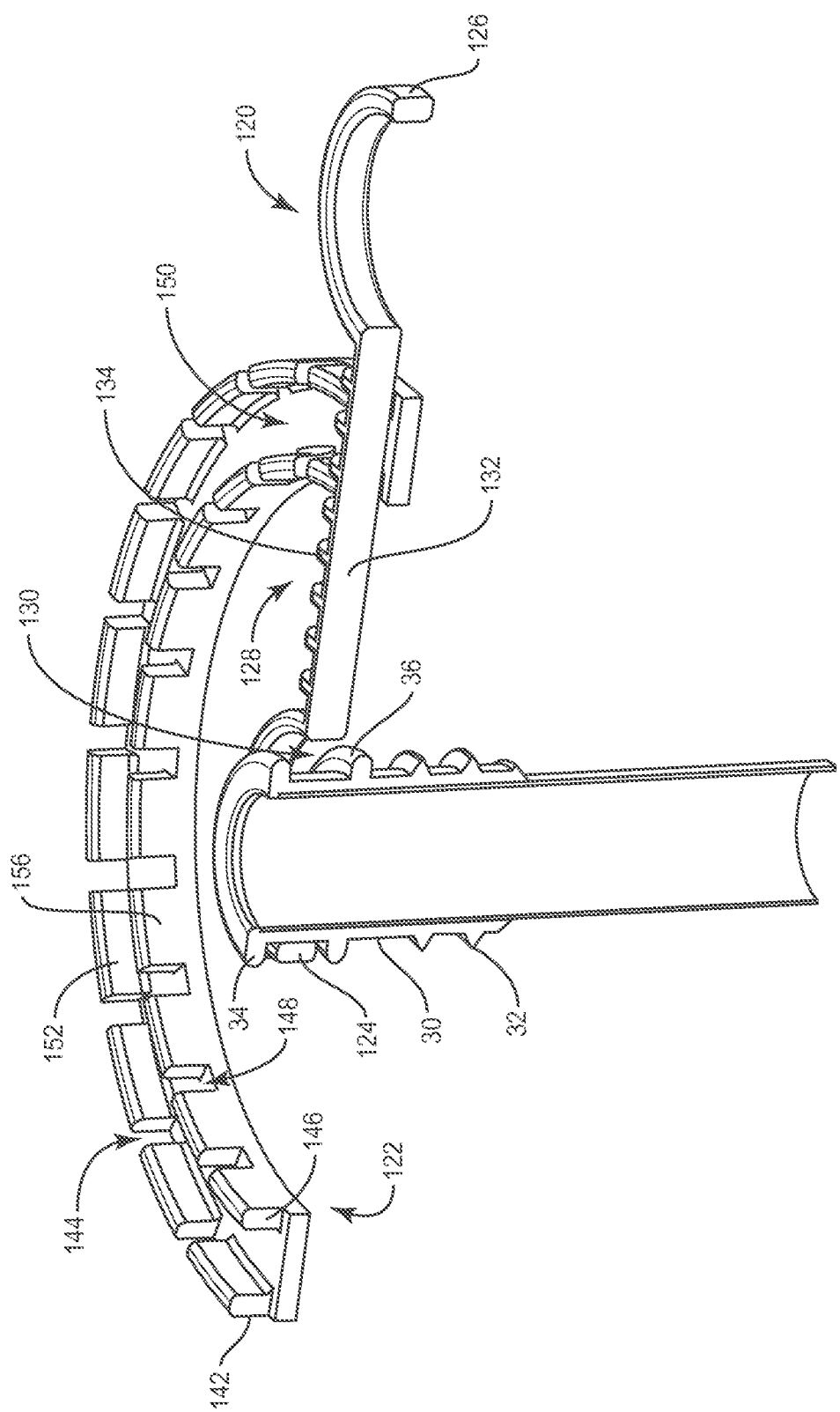
FIG. 2 is a perspective, cross sectional view of components of one embodiment of the system shown in FIG. 1.
Figure 3:
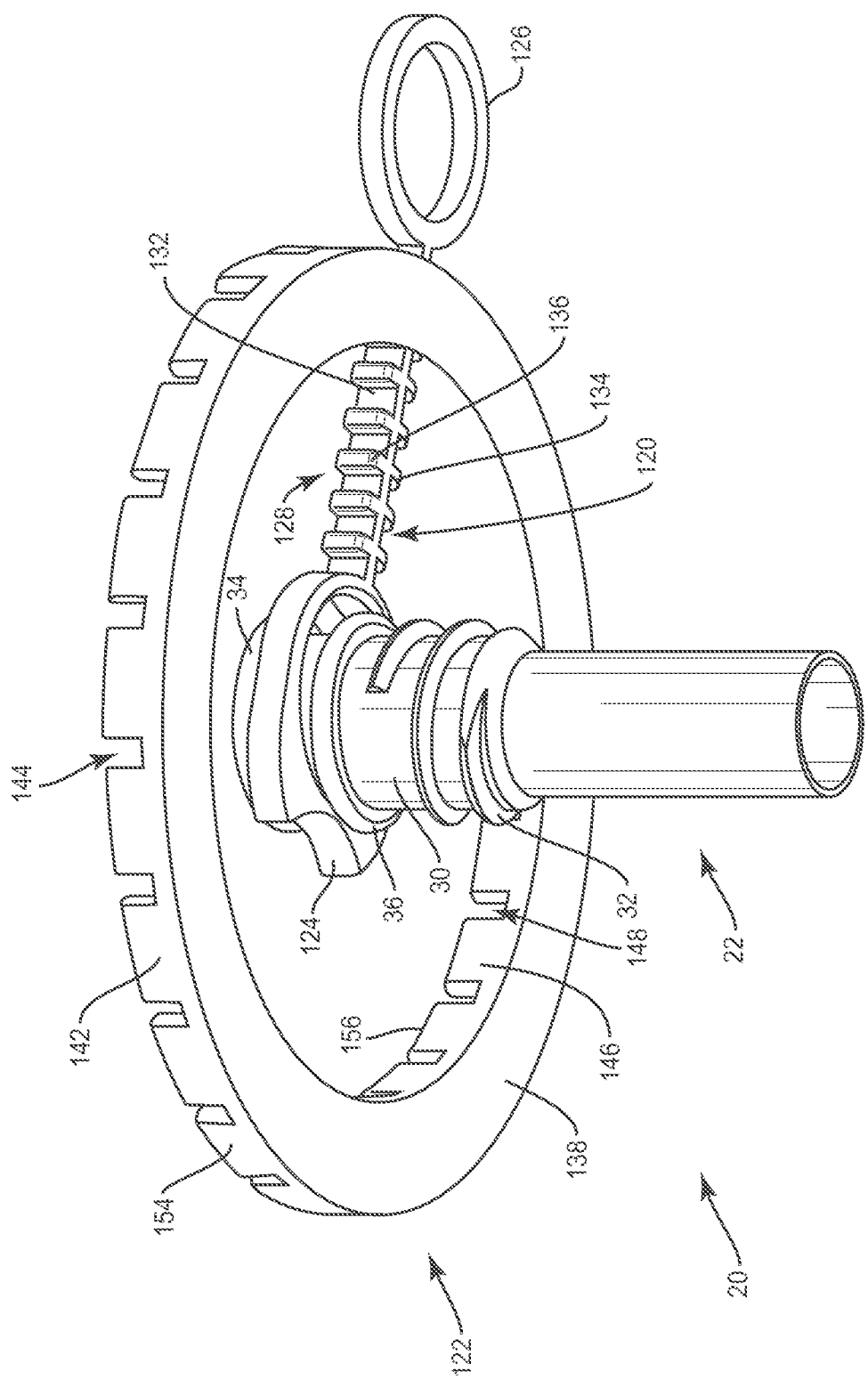
FIG. 3 is a bottom, perspective view of components of one embodiment of the system shown in FIG. 1.
Figure 4:
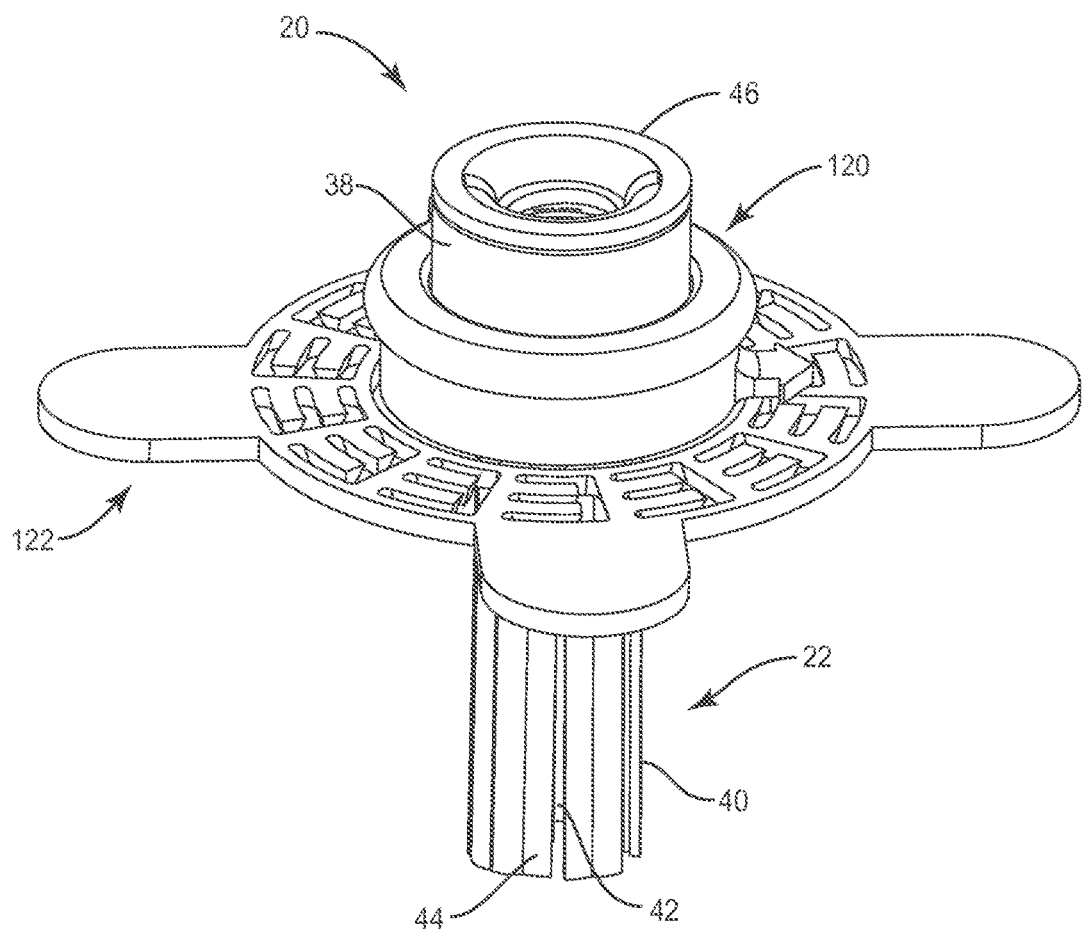
FIG. 4 is a top, perspective view of components of one embodiment of a surgical system in accordance with the principles of the present disclosure.

Patient attachable ring 122 shown in FIGS. 1-3 is provisionally fixed to the skin of the patient by applying an adhesive or other sticky or tacky material to the bottom surface of patient attachable ring 122 and contacting the bottom surface of patient attachable ring 122 with the skin of the patient. Engagement portion 124 of collar 120 shown in FIGS. 1-3 is positioned between proximal flange 34 and distal flange of sleeve 30 to attach collar 120 to cannula 22. First locking element 128 of collar 120 engages second locking element 140 of patient attachable ring 122 in the manner discussed above to provisionally fix collar 120 relative to patient attachable ring 122 in a first configuration.

Collar 120 may be moved relative to patient attachable ring 122 by disengaging first locking element 128 of collar 120 from second locking element 140 of patient attachable ring 122 by removing body 132 of first locking element 128 from first and second slots 144, 148 of second locking element 140 at fixed junction 175. Collar 120 may be moved axially relative to patient attachable ring 122 or collar 120 may be moved radially relative to patient attachable ring 122 to adjust the position of cannula 22 relative to patient attachable ring 122. Collar 120 may be moved axially relative to patient attachable ring 122 by moving collar 120 from the first configuration to a second configuration. In particular, collar 120 may be moved axially toward the inner surface of patient attachable ring 122 that defines pathway 176 or axially away from the inner surface of patient attachable ring 122 that defines pathway 176. After collar 120 is moved axially relative to patient attachable ring 122, body 132 may be inserted into the same first and second slots 144, 148 that were used to provisionally fix collar 120 relative to patient attachable ring 122 in the first configuration such that a fifth one of first projections 134 and a fifth one of second projections may engage inner surface 152 of first wall 142, a sixth one of first projections 134 and a sixth one of second projections 136 engage outer surface 154 of first wall 142, a seventh one of first projections 134 and a seventh one of second projections 136 engages an inner surface 156 of second wall 146 and an eighth one of first projections 134 and an eighth one of second projections 136 engage outer surface 158 of second wall 146.

Alternatively, collar 120 may be moved radially about patient attachable ring 122 to move collar 120 from the first configuration to a second configuration. After collar 120 is moved radially about patient attachable ring 122, body 132 may be inserted into different first and second slots 144, 148 than those that were used to provisionally fix collar 120 relative to patient attachable ring 122 in the first configuration such that first locking element 128 of collar 120 engages second locking element 140 of patient attachable ring 122 at fixed junction 175 in the manner discussed above.

In some embodiments, cannula 22 includes a light source, such as, for example, a light emitting diode that is configured to illuminate a working channel defined by an inner surface or inner surfaces of cannula 22.

Concerning collar 120 shown in FIGS. 6 and 7 and patient attachable ring 122 shown in FIGS. 8 and 9, collar 120 may be positioned over holding member 38 and a top nut 46 of system 20 such that holding member 38 and top nut 46 are movably disposed in pathway 160 of collar 120, as shown in FIG. 5. Holding member 38 and top nut 46 may be moved along axis L1 in a proximal direction until an overhang 206 of holding member 38 shown in FIG. 5 engages a ledge 208 of collar 120 shown in FIG. 5.

Patient attachable ring 122 shown in FIGS. 8 and 9 may be affixed to the skin of the patient. An adhesive or other tacky or sticky material may be applied to the bottom surface of patient attachable ring 122 and/or the lower surface of at least one of straps 178 of patient attachable ring 122 before affixing of patient attachable ring 122 to the skin of the patient. In some embodiments, the bottom surface of the patient attachable ring 122 and/or the lower surface of at least one of straps 178 may be equipped with tape having a sticky or tacky material covered by a removable cover strip that once removed exposes the sticky or tacky material which can be used to adhere to the patient's skin. The assembly of holding member 38, cannula 22, top nut 46 and collar 120 is positioned relative to patient attachable ring 122 such that cannula 22 extends through pathway 176 of patient attachable ring 122.

First locking element 166 of collar 120 is positioned to engage a respective one of second locking elements 168 of patient attachable ring 122 to fix the assembly of holding member 38, cannula 22, top nut 46 and collar 120 relative to patient attachable ring 122. In particular, first locking element 166 is positioned relative to the respective one of second locking elements 168 such that first locking element 166 is aligned with groove 182 of second locking element 168 at fixed junction 175. First locking element 166 is moved such that second portion 172 of first locking element 166 moves through opening 202 in groove 182.

First locking element 166 is then translated within groove 182 until first locking element 166 is aligned with one of grooves 180 of first locking element 166, such as, for example, one of grooves 180A, 180B, 180C shown in FIG. 10. First locking element 166 is then slid into one of grooves 180A, 180B, 180C. Which of grooves 180A, 180B, 180C the surgeon selects to slide first locking element 166 into may depend upon, for example, how close the surgeon desires the assembly of holding member 38, cannula 22, top nut 46 and collar 120 to be relative to patient attachable ring 122, such as, for example, inner wall 190 of patient attachable ring 122. For example, if the surgeon desires the assembly of holding member 38, cannula 22, top nut 46 and collar 120 to be positioned closer to inner wall 190, the surgeon will slide first locking element 166 into groove 180A and if the surgeon desires the assembly of holding member 38, cannula 22, top nut 46 and collar 120 to be positioned farther from wall 190, the surgeon will slide first locking element 166 into groove 180C. In that patient attachable ring 122 comprises a plurality of sets of second locking elements 168 and/or a plurality of grooves 182 the surgeon can select the second locking element 168 and/or groove 182 that best positions the assembly of holding member 38, cannula 22, top nut 46 and collar 120 to be relative to patient attachable ring 122 when first locking element 166 is disposed in the selected groove.

First locking element 166 may be removed from the respective one of second locking elements 168 and positioned within another one of second locking elements 168 at fixed junction 175 in the same manner first locking element 166 was positioned relative to the respective one of second locking elements 168 at fixed junction 175. That is, first locking element 166 may be positioned relative to the other one of second locking elements 168 such that first locking element 166 is aligned with groove 182 of second locking element 168 at fixed junction 175. First locking element 166 may be moved such that second portion 172 of first locking element 166 moves through opening 202 in groove 182 of the another one of second locking elements 168 at fixed junction 175. First locking element 166 may then translated within groove 182 until first locking element 166 is aligned with one of grooves 180, such as, for example, one of grooves 180A, 180B, 180C of the another one of second locking elements 168. First locking element 166 may then slid into one of grooves 180A, 180B, 180C of the other one of second locking elements 168. In some embodiments, cannula 22 includes a light source, such as, for example, a light emitting diode that is configured to illuminate a working channel defined by an inner surface or inner surfaces of cannula 22. In some embodiments, cannula 22 is expandable such that cannula 22 is movable from a first configuration in which members 40, 42, 44 extend parallel to one another and cannula 22 has a first maximum diameter to a second configuration in which members 40, 42, 44 extend transverse to one another and cannula 22 has a second maximum diameter that is greater than the first maximum diameter.

It is envisioned that the use of microsurgical and image guided technologies may be employed to access, view and repair spinal deterioration or damage, with the aid of cannula 22. It is contemplated that a surgical procedure may employ other instruments that can be mounted with cannula 22, such as, for example, nerve root retractors, tissue retractors, forceps, cutter, drills, scrapers, reamers, rongeurs, taps, cauterization instruments, irrigation and/or aspiration instruments, illumination instruments, inserter instruments and/or separators, such as, for example, one or more burrs.

Cannula 22 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
an expandable cannula including a first end, an opposite second end, and at least a first wall member and a second wall member extending between the first end and the second end, the first wall member and the second wall member being moveable between an unexpanded configuration and an expanded configuration;
a collar coupled to the expandable cannula adjacent the first end thereof, the collar comprising an extension portion and a first locking element provided on the extension portion; and
a patient attachable ring comprising a first passageway and a second locking element, the first passageway having a central axis and being configured to receive portions of the expandable cannula therethrough, and the first locking element being configured to engage the second locking element to control the movement of the cannula within the patient attachable ring, the second locking element including a radial groove extending in a radial direction with respect to the central axis, and a first circumferential groove extending in a circumferential direction with respect to the central axis, the radial groove and the first circumferential groove communicating with one another, and a portion of the first locking element being moveable within the radial groove and the first circumferential groove to facilitate corresponding radial and circumferential movement of the first locking element relative to the central axis, the expandable cannula being selectively positionable from at least a first cannula position to a second cannula position via corresponding movement of the first locking element from a first position within the second locking element to a second position within the second locking element;
wherein the first wall member includes a first longitudinal axis, and the first longitudinal axis is moveable with respect to the central axis of the first passageway via movement of the expandable cannula between the unexpanded configuration and the expanded configuration, and via movement of the expandable cannula due to selective positioning of the first locking element within the second locking element.

2. The surgical instrument as recited in claim 1, wherein the first and second locking elements are detachable from one another.

3. The surgical instrument as recited in claim 1, wherein the second locking element includes a second circumferential groove extending in a circumferential direction with respect to the central axis, the radial groove, the first circumferential groove, and the second circumferential groove communicating with one another, the first locking element being moveable within the radial groove, the first circumferential groove, and the second circumferential groove.

4. The surgical instrument as recited in claim 3, wherein the first and second locking elements define a sliding dovetail joint.

5. The surgical instrument as recited in claim 3, wherein the first locking element is a tapered tenon and the second locking element is a mortise that slidingly engages the tenon such that the tenon and the mortise define a sliding dovetail joint.

6. The surgical instrument as recited in claim 3, wherein the first locking element is a tapered tenon and the radial groove, the first circumferential groove, and the second circumferential groove of the second locking element each comprise a mortise that are in communication with one another, the tenon slidingly engaging one of the mortises to define a sliding dovetail joint.

7. The surgical instrument as recited in claim 3, further comprising a plurality of second locking elements positioned around the patient attachable ring.

8. The surgical instrument as recited in claim 1, wherein the collar engages the expandable cannula to prevent axial translation of the collar relative the expandable cannula along the central axis.

9. The surgical instrument of claim 1, wherein the cannula comprises a light source.

10. A method of using a cannula positioning system, the method comprising:
   providing a system including:
      an expandable cannula including a first end, an opposite second end, and at least a first wall member and a second wall member extending between the first end and the second end, the first wall member and the second wall member being moveable between an unexpanded configuration and an expanded configuration;
      a collar coupled to the expandable cannula adjacent the first end thereof, the collar comprising an extension portion and a first locking element provided on the extension portion; and
      a patient attachable ring comprising a first passageway and a second locking element, the first passageway having a central axis and being configured to receive portions of the expandable cannula therethrough, and the first locking element being configured to engage the second locking element to control the movement of the expandable cannula within the patient attachable ring, the second locking element including a radial groove extending a radial direction with respect to the central axis, and a first circumferential groove extending in a circumferential direction with respect to the central axis, the radial groove and the first circumferential groove communicating with one another, and a portion of the first locking element being moveable within the radial groove and the first circumferential groove to facilitate corresponding radial and circumferential movement of the first locking element relative to the central axis;
   engaging the first and second locking elements together to secure the position of the expandable cannula within the patient attachable ring;
   moving the expandable cannula between the unexpanded configuration and the expanded configuration; and
   selectively positioning the first locking element from a first position within the second locking element to a second position within the second locking element to correspondingly move the expandable cannula from a first cannula position to a second cannula position;
   wherein the first wall member includes a first longitudinal axis, and the first longitudinal axis is moveable with respect to the central axis of the first passageway via the movement of the expandable cannula between the unexpanded configuration and the expanded configuration, and via movement of expandable cannula due to the selective positioning of the first locking element within the second locking element.

11. The method of claim 10, wherein the first and second locking elements define a sliding dovetail joint.

12. The method of claim 10, wherein the first and second locking elements are detachable from one another.

13. The method of claim 10, wherein the second locking element includes a second circumferential groove extending in a circumferential direction with respect to the central axis, the radial groove, the first circumferential groove, and the second circumferential groove communicating with one another, the first locking element being moveable within the radial groove, the first circumferential groove, and the second circumferential groove.

14. The method of claim 13, wherein the first and second locking elements define a sliding dovetail joint.

15. The method of claim 13, wherein the first locking element is a tapered tenon and the second locking element is a mortise that slidingly engages the tenon such that the tenon and the mortise define a sliding dovetail joint.

16. The method of claim 13, wherein the first locking element is a tapered tenon and the radial groove, the first circumferential groove, and the second circumferential groove of the second locking element each comprise a mortise that are in communication with one another, the tenon slidingly engaging one of the mortises to define a sliding dovetail joint.

17. The method of claim 13, further comprising a plurality of second locking elements positioned around the patient attachable ring.

* * * * *